(12) United States Patent
Nishii et al.

(10) Patent No.: US 6,517,870 B1
(45) Date of Patent: Feb. 11, 2003

(54) ORAL FORMULATION COMPRISING BIGUANIDE AND AN ORGANIC ACID

(75) Inventors: Hiroyuki Nishii, Osaka (JP); Hirohisa Kobayashi, Osaka (JP); Kazuya Otoda, Takarazuka (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/674,150

(22) PCT Filed: Apr. 26, 1999

(86) PCT No.: PCT/JP99/02192

§ 371 (c)(1),
(2), (4) Date: Oct. 27, 2000

(87) PCT Pub. No.: WO99/55320

PCT Pub. Date: Nov. 4, 1999

(30) Foreign Application Priority Data

Apr. 29, 1998 (JP) .............................. 10-136126

(51) Int. Cl.[7] .............................. A61K 9/08; A61K 9/14; A61K 9/20

(52) U.S. Cl. .................. 424/489; 424/440; 424/441; 424/464; 424/439; 514/784; 514/866; 514/974

(58) Field of Search ................................ 424/489, 464, 424/465, 455, 439, 440, 441

(56) References Cited

U.S. PATENT DOCUMENTS

| 4,089,957 A | 5/1978 | Jonsson ................. 424/248.56 |
| 5,260,275 A | 11/1993 | Cooper et al. ................. 514/12 |
| 5,324,748 A | 6/1994 | Horrobin ..................... 514/560 |
| 6,031,004 A | * 2/2000 | Timmins et al. ............ 514/635 |

FOREIGN PATENT DOCUMENTS

| DE | A2 124256 | 11/1972 | |
| DE | 2124256 | * 11/1972 | ............ A61K/2/36 |
| EP | A 390369 | 10/1990 | |
| EP | A20390369 | 10/1990 | |
| EP | A30390369 | 10/1990 | |
| GB | A1 539076 | 1/1979 | |
| JP | A60246325 | 6/1985 | |
| JP | A1242524 | 9/1989 | |
| JP | A899904 | 4/1996 | |
| JP | A1036252 | 2/1998 | |
| WO | A19827982 | 2/1998 | |
| WO | A9 827982 | 7/1998 | |

OTHER PUBLICATIONS

Patent Abstracts of Japan, vol. 10, No. 120 (C–343), Abstract of JP 60 246325 A Dec. 6, 1985.

* cited by examiner

Primary Examiner—James M. Spear
(74) Attorney, Agent, or Firm—Birch, Stewart, Kolasch & Birch, LLP

(57) ABSTRACT

An oral formulation comprising a biguanide and an organic acid has less unpleasant tastes such as bitterness and saltiness.

12 Claims, No Drawings

ORAL FORMULATION COMPRISING BIGUANIDE AND AN ORGANIC ACID

This application is the national phase under 35 U.S.C. §371 of PCT International Application No. PCT/JP99/02192 which has an International filing date of Apr. 26, 1999, which designated the United States of America.

TECHNICAL FIELD

The present invention relates to an oral fomulation comprising a biguanide and an organic acid.

BACKGROUND OF THE INVENTION

Biguanides such as metformin have unpleasant tastes such as bitterness and saltiness. The dosages of metformin are about 250 mg per dose in Japan and about 850 mg per dose in United States of America. In spite of such big dosages, only tablets are on sale at present.

There are several known methods for masking bitterness of bitter drugs, for instance, for solid formulations, sugar coated tablets, film coated tablets, capsules and the like are useful. Powders, fine granules and granules are formulated with sweetening agents or flavors; microcapsules, non-enteric coated formulation, spray-dried formulation with low melting point wax, formulation with lecithin (JP 62-265234-A) and the like may also be used. For solutions, there are formulations with water-insoluble high molecular weight compound such as ethylcellulose and hydroxypropylmethylcellulose phthalate (JP 52-41214-A); formulations with acidic phospholipids or lyso-phospholipids (JP 7-67552-A); and formulations with a large amount of citric acid (JP 4-58452-B).

DISCLOSURE OF THE INVENTION

The inventors of the present invention have intensively carried out research, and found that an oral formulation comprising a biguanide and an organic acid has less unpleasant tastes such as bitterness and saltiness. Thus, the present invention has been accomplished.

The present inventions includes:

[1] An oral formulation comprising a biguanide and an organic acid.

[2] An oral formulation comprising a biguanide, an organic acid and a sweetening agent.

[3] An oral formulation according to [1] or [2] wherein the biguanide is metformin or a pharmaceutical salt thereof.

[4] An oral formulation according to any one of [1] to [3] wherein the organic acid is malic acid, citric acid, tartaric acid or mixture thereof.

[5] An oral formulation according to any one of [1] to [4] wherein the sweetening agent is aspartame™, saccharine, saccharine sodium, stevioside or mixture thereof.

[6] An oral formulation according to any one of [1] to [5] wherein the ratio (w/w) of the biguanide to the organic acid is 1:0.1 to 1:50.

[7] An oral formulation according to any one of [2] to [6] wherein the ratio (w/w) of the biguanide to the sweetening agent is 1:0.001 to 1:10

[8] An oral formulation according to any one of [1] to [7] wherein the formulation is solution, jelly, gum drops, dry syrup, powders, fine granules or granules.

[9] An oral formulation according to any one of [1] to [8] wherein the pH of the solution is 3.5 to 6 in case that the formulation is solution, and the pH of the solution which is formed by dissolving or dispersing the formulation to 10 times more (w/w) volume of water, is 3.5 to 6 in case that the formulation is not solution.

DETAILED DESCRIPTION OF THE INVENTION

"Biguanide" includes compounds having a biguanide structure such as metformin, buformin, phenformin and pharmaceutically acceptable salts thereof.

"Organic acid" includes malic acid, citric acid, tartaric acid, ascorbic acid, succinic acid, fumaric acid, maleic acid, gluconic acid, glucuronic acid and mixtures thereof. Preferable organic acids are organic acids having 2 or 3 carboxyl groups such as malic acid, citric acid and tartaric acid, more preferably malic acid. The ratio (w/w) of the biguanide to the organic acid is, for example, 1:0.01 to 1:50, preferably 1:0.02 to 1:10, more preferably 1:0.05 to 1:1. In the case of malic acid, the preferable ratio (w/w) of the biguanide to malic acid is 1:0.05 to 1:0.5.

"Sweetening agent" includes aspartame™, saccharin, saccharin sodium, stevioside, thaumatin, erythritol, sorbitol, xylitol, glycerin and mixtures thereof. Preferable sweetening agents are aspartame™, saccharin, saccharin sodium and stevioside. The ratio (w/w) of the biguanide to the sweetening agent is, for example, 1:0.001 to 1:10, preferably 1:0.02 to 1:1.

When the formulation is a solution, preferably the pH of the solution is 3.5 to 6, more preferably 4 to 6, to decrease the unpleasant tastes and to keep the biguanide stable. If the formulation is not a solution, the preferable pH of the solution or dispersion which is formed by dispersing the formulation in water (1 part of the formulation to 10 parts of water, by weight), is 3.5 to 6, more preferably 4 to 6; This is in order to decrease the unpleasant tastes and to keep the biguanide stable.

"Oral formulation" includes solution, jelly, gum drops, dry syrup, powders, fine granules and granules. Preferably the formulation is not in the form of tablets.

The formulation of the present invention may include at pharmaceutically acceptable non-toxic and inactive additives. Additives include excipients such as corn starch, potato starch, white sugar, mannitol, xylitol, sorbitol, talc, kaolin, calcium monohydrogen phosphate, calcium sulfate, calcium carbonate, crystalline cellulose; lubricants such as magnesium stearate and potassium stearate; disintegrators such as carboxymethylcellulose calcium and low substituted hydroxymethylcellulose; binders such as hydroxypropylcellulose, hydroxypropylmethylcellulose, polyvinypyrrolidone, gelatin, methylcellulose, Arabia gum and polyvinylalcohol; coloring agents; correctives; adsorbents; preservatives; stabilizers; moistening agents; de-charging agents; pH adjusters; and the like.

The formulation may include flavors such as lemon, orange, grapefruit, pine, banana, chocolate and yogurt to decrease the unpleasant tastes more.

The formulation of the present invention can be prepared by well known methods. In the case of solid formulations, the formulation can be prepared, for example, by extruding granulation methods, crushing granulation methods, dry granulation methods, fluidized bed granulation methods, tumbling granulation methods, high shear mixing granulation methods, wet compression methods, direct compression methods and the like.

The formulation of the present invention will contain the conventional amounts of active ingredient (biguanide) and will be used in conventional manner to administer doses in accordance with normal practice by routes and according to dosage regimes which are familiar to pharmacologists and medical practitioners.

The present invention will be described in detail below, referring to Examples and Experiments, which are not limitative of the present invention.

EXAMPLE 1

Solution of metformin hydrochloride

| Ingredient | weight % |
|---|---|
| Metformin hydrochloride | 5% |
| Malic acid | 0.8% |
| Aspartame ™ | 0.3% |
| Lemon flavor | 0.1% |
| Purified water | 93.8% |

5% Solution of metformin hydrochloride is prepared by dissolving metformin hydrochloride, malic acid, aspartame™ and lemon flavor into purified water.

EXAMPLE 2

Solution of metformin hydrochloride

| Ingredient | weight % |
|---|---|
| Metformin hydrochloride | 5% |
| Malic acid | 0.8% |
| Saccharin sodium | 1% |
| Lemon flavor | 0.1% |
| Purified water | 93.1% |

5% Solution of metformin hydrochloride is prepared by dissolving metformin hydrochloride, malic acid, saccharine sodium and lemon flavor into purified water.

EXAMPLE 3

Solution of metformin hydrochloride

| Ingredient | weight % |
|---|---|
| Metformin hydrochloride | 5% |
| Citric acid | 2% |
| Aspartame ™ | 0.3% |
| Lemon flavor | 0.1% |
| Purified water | 92.6% |

5% Solution of metformin hydrochloride is prepared by dissolving metformin hydrochloride, citric acid, aspartame™ and lemon flavor into purified water.

EXAMPLE 4

Solution of metformin hydrochloride

| Ingredient | weight % |
|---|---|
| Metformin hydrochloride | 5% |
| Malic acid | 1.5% |
| Saccharin sodium | 0.25% |
| Erythritol | 10% |
| Lemon flavor | 0.1% |
| Purified water | 83.15% |

5% Solution of metformin hydrochloride is prepared by dissolving metformin hydrochloride, malic acid, saccharin sodium, erythritol land lemon flavor into purified water.

EXAMPLE 5

Solution of metformin hydrochloride

| Ingredient | weight % |
|---|---|
| Metformin hydrochloride | 5% |
| Malic acid | 1.5% |
| Aspartame ™ | 0.2% |
| Sorbitol | 6% |
| Grapefruit flavor | 0.1% |
| Purified water | 87.2% |

5% Solution of metformin hydrochloride is prepared by dissolving metformin hydrochloride, malic acid, aspartame™, sorbitol and grapefruit flavor into purified water.

EXAMPLE 6

Solution of metformin hydrochloride

| Ingredient | weight % |
|---|---|
| Metformin hydrochloride | 5% |
| Malic acid | 1.5% |
| Saccharin | 0.03% |
| Glycerin | 10% |
| Lemon flavor | 0.1% |
| Purified water | 83.37% |

5% Solution of metformin hydrochloride is prepared by dissolving metformin hydrochloride, malic acid, saccharin, glycerin and lemon flavor into purified water.

EXAMPLE 7

Solution of metformin hydrochloride

| Ingredient | weight % |
|---|---|
| Metformin hydrochloride | 5% |
| Malic acid | 1.5% |
| Saccharin sodium | 0.25% |
| Saccharin | 0.03% |
| Lemon flavor | 0.1% |
| Purified water | 93.12% |

5% Solution of metformin hydrochloride is prepared by dissolving metformin hydrochloride, malic acid, saccharin sodium, saccharin and lemon flavor into purified water.

EXAMPLE 8

Dry syrup of metformin hydrochloride

| Ingredient | Amount |
|---|---|
| Metformin hydrochloride | 500 g |
| Malic acid | 80 g |
| Saccharin sodium | 25 g |
| Erythritol | 865 g |
| Polyvinylpyrrolidone K30 | 30 g |
| Total | 1500 g |

Metformin hydrochloride, malic acid, saccharin sodium, erythritol and polyvinylpyrrolidone K30 are mixed with 200 g of mixture of purified water and ethanol (1:1 (w/w)) to give wet solid. 33% Dry syrup of metformin hydrochloride is prepared by milling the wet solid with a granulation mill to adjust the size of the granules, followed by drying.

EXAMPLE 9

Jelly of metformin hydrochloride

| Ingredient | weight % |
|---|---|
| Metformin hydrochloride | 5% |
| Gelatin | 0.5% |
| Malic acid | 0.8% |
| Aspartame ™ | 0.3% |
| Lemon flavor | 0.1% |
| Purified water | 93.3% |

Jelly of metformin hydrochloride is prepared by dissolving or dispersing metformin hydrochloride, malic acid, aspartame™ and lemon flavor into gelatin solution which is made by dissolving gelatin to purified water over 80° C., followed by cooling.

EXAMPLE 10

Fine granules of buformin hydrochloride

| Ingredient | Amount |
|---|---|
| Buformin hydrochloride | 100 g |
| Mannitol | 300 g |
| Lactose | 300 g |
| Corn starch | 150 g |
| Malic acid | 90 g |
| Aspartame ™ | 30 g |
| Methyl cellulose | 30 g |
| Total | 1000 g |

Buformin hydrochloride, mannitol, lactose, corn starch, malic acid, aspartame™ and methylcellulose are mixed with 200 g of purified water to give wet solid. 10% Fine granules of buformin hydrochloride are prepared by granulating the wet solid with a basket granulation mill, followed by drying.

EXAMPLE 11

Gum drops of buformin hydrochloride

| Ingredient | Amount |
|---|---|
| Buformin hydrochloride | 100 mg |
| Gelatin | 600 mg |
| Citic acid | 100 mg |
| Saccharin sodium | 25 mg |
| Sorbitol | 1550 mg |
| Lemon flavor | 25 mg |
| Purified water | 600 mg |
| Total | 3000 mg |

Gum drops of buformin hydrochloride are prepared by dissolving or dispersing buformin hydrochloride, citric acid, saccharin sodium, sorbitol and lemon flavor into gelatin solution which is made by dissolving gelatin to purified water over 80° C., followed by molding the mixture and cooling.

EXAMPLE 12

Powders of buformin hydrochloride

| Ingredient | Amount |
|---|---|
| Buformin hydrochloride | 100 mg |
| Mannitol | 560 mg |
| Corn starch | 200 mg |
| Citric acid | 100 mg |
| Aspartame ™ | 30 mg |
| Magnesium stearate | 10 mg |
| Total | 1000 mg |

10% powders of buformin hydrochloride are prepared by mixing buformin hydrochloride, mannitol, corn starch, citric acid, aspartame™ and magnesium stearate.

EXAMPLE 13

Solutions of Metformin Hydrochloride at Various pH

Using the same amount of each ingredient of Example 1, 5% solutions of metformin hydrochloride at various pH are prepared by dissolving or dispersing metformin hydrochloride, malic acid, aspartame™ and lemon flavor into about 80% of purified water, followed by adjusting pH of the solution to pH 2, 3, 3.5, 4, 5 or 6 using dilute hydrochloric acid or dilute sodium hydroxide solution and adding more purified water.

REFERENCE EXAMPLE 1

Solution of metformin hydrochloride

| Ingredient | weight % |
|---|---|
| Metformin hydrochloride | 5% |
| Purified water | 95% |

5% Solution of metformin hydrochloride is prepared by dissolving metformin hydrochloride into purified water.

Experiment 1

Tasting Experiment

Tasting experiments on the solutions of Examples 1 to 3 and Reference example 1 were carried out with 20 panelists. The numbers of panelists who felt the solution "not bitter", "a little bitter" and "very bitter" are shown in Table 1.

TABLE 1

| Solution | "not bitter" | "a little bitter" | "very bitter" |
| --- | --- | --- | --- |
| Example 1 | 11 | 8 | 1 |
| Example 2 | 10 | 9 | 1 |
| Example 3 | 11 | 8 | 1 |
| Reference example 1 | 0 | 2 | 18 |

Tasting experiments on the solutions of Examples 4 to 7 were also carried out, with satisfactory results.

Experiment 2

Tasting and Stability Experiments

Tasting and stability experiments on the solutions at various pH of Example 13 were carried out, in the same manner as Experiment 1. A stability experiment was carried out by measuring the remaining amount of metformin in the solutions with HPLC after heating the solutions in vials at 60 C. for 2 weeks. The results are shown in Table 2.

TABLE 2

| pH | taste | remaining amount (%) |
| --- | --- | --- |
| 2 | very sour | 78 |
| 3 | sour | 86 |
| 3.5 | good | 94 |
| 4 | good | 96 |
| 5 | good | 98 |
| 6 | good | 100 |
| 7 | very bitter | 98 |

Metformin hydrochloride is not stable below pH 3.5, and the solution tastes sour. The solution over pH 7 has bitterness.

Normally we feel bitterness most in solution formulation. Therefore these experiments on the solutions indicate that other formulations such as jelly, gum drops, dry syrup, powders, fine granules and granules have less unpleasant tastes as well.

The present invention provides an oral formulation of biguanide with less unpleasant tastes. With this invention, people in every age group, for example, elderly people and little children can easily have sufficient amount of biguanide.

What is claimed is:

1. An oral formulation comprising a biguanide and an organic acid, wherein the organic acid is a member selected from the group consisting of malic acid, citric acid, tartaric acid, succinic acid, fumaric acid, maleic acid, gluconic acid, glucuronic acid and mixtures thereof.

2. An oral formulation according to claim 1, wherein the organic acid is a member selected from the group consisting of malic acid, citric acid, tartaric acid and mixtures thereof.

3. An oral formulation according to claim 1, further comprising a sweetening agent.

4. An oral formulation according to claim 1, further comprising L-aspartyl-L-phenylalanine methyl ester, saccharine, saccharine sodium,'stevioside or a mixture thereof.

5. An oral formulation according to claim 3, wherein the ratio (w/w) of the biguanide to the sweetening agent is 1:0.001 to 1:10.

6. An oral formulation according to claim 1, wherein the biguanide is a member selected from the group consisting of metformin, buformin, phenformin and pharmaceutically acceptable salts thereof.

7. An oral formulation according to claim 1, wherein the biguanide is metformin or a pharmaceutically acceptable salt thereof.

8. An oral formulation according to claim 1, wherein the ratio (w/w) of the biguanide to the organic acid is 1:0.01 to 1:50.

9. An oral formulation according to any one of claims 1 to 8, wherein the formulation is a member selected from the group consisting of a solution, jelly, gum drops, dry syrup, powders, fine granules or granules.

10. An oral formulation according to claim 9, which is in the form of a solution wherein the pH of the solution is 3.5 to 6.

11. An oral formulation according to claim 9, which is not in the form of a solution and the pH of the solution or dispersion which is formed by dispersing 1 part of the formulation in 10 parts by weight of water is 3.5 to 6.

12. A method of masking an unpleasant taste of a biguanide, comprising adding an organic acid to an oral formulation containing the biguanide.

* * * * *